(12) United States Patent
Thrower et al.

(10) Patent No.: US 8,247,352 B2
(45) Date of Patent: Aug. 21, 2012

(54) METHOD OF INHIBITING ETHYLENE PRODUCTION IN PLANTS

(75) Inventors: Julie Thrower, Silver Spring, MD (US); Judith Klinman, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1139 days.

(21) Appl. No.: 11/885,915

(22) PCT Filed: Mar. 10, 2006

(86) PCT No.: PCT/US2006/008584
§ 371 (c)(1),
(2), (4) Date: May 9, 2008

(87) PCT Pub. No.: WO2006/099129
PCT Pub. Date: Sep. 21, 2006

(65) Prior Publication Data
US 2009/0011939 A1   Jan. 8, 2009

Related U.S. Application Data

(60) Provisional application No. 60/660,809, filed on Mar. 11, 2005.

(51) Int. Cl.
*A01N 43/60* (2006.01)
*A01N 43/54* (2006.01)
*A01N 43/40* (2006.01)
*A01N 43/80* (2006.01)
*A01N 43/56* (2006.01)
*A01N 43/36* (2006.01)
*A01N 43/10* (2006.01)
*A01N 43/08* (2006.01)

(52) U.S. Cl. ........ 504/235; 504/239; 504/244; 504/269; 504/271; 504/275; 504/280; 504/283; 504/289; 504/294

(58) Field of Classification Search .................. None
See application file for complete search history.

(56) References Cited

U.S. PATENT DOCUMENTS

| 4,372,776 | A | * | 2/1983 | Day et al. .................. 504/289 |
| 4,452,625 | A | * | 6/1984 | Lurssen et al. ............. 504/139 |
| 5,041,612 | A |   | 8/1991 | Lunkenheimer et al. |
| 5,801,119 | A |   | 9/1998 | Venburg et al. |

OTHER PUBLICATIONS

Romera et al. (Ethylene production by Fe-deficient roots and its involvement in the regulation of Fe-deficiency stress responses by strategy I plants (Annals of Botany, London, 1999, 83(1), 51-55).*
International Search Report mailed Nov. 27, 2006, for PCT Application No. PCT/US06/08584 filed Mar. 10, 2006, 1 page.
International Preliminary Report on Patentability received for PCT Patent Application No. PCT/US2006/008584, issued on Sep. 12, 2007, 4 pages.

* cited by examiner

*Primary Examiner* — Alton Pryor
(74) *Attorney, Agent, or Firm* — Morrison & Foerster LLP (57) ABSTRACT

Methods of inhibiting ethylene production in a plant are provided that involve contacting a plant or plant part with an inhibitor of 1-aminocyclopropane-1-carboxylic acid oxidase (ACCO). The methods can be used to delay fruit and vegetable ripening, flower opening, or senescence of cut flowers. Also described are kits including an ACCO inhibitor and a floral preservative.

12 Claims, 3 Drawing Sheets

METHOD OF INHIBITING ETHYLENE PRODUCTION IN PLANTS

CROSS-REFERENCE TO RELATED APPLICATIONS

This application is a U.S. national phase application of International Application No. PCT/US2006/008584, filed Mar. 10, 2006, which claims priority to U.S. Provisional Patent Application No. 60/660,809, filed Mar. 11, 2005, the contents of which are hereby incorporated by reference into the present disclosure in their entirety.

GOVERNMENT SUPPORT

This subject matter described herein was made with government support under GM 25765 awarded by the National Institutes of Health. The government has certain rights in the subject matter described herein.

FIELD

Described herein are methods for controlling the rate of ripening and senescence of economically valuable plants and plant parts. Specifically, described herein are methods of inhibiting ethylene production in plants and plant parts, and particularly to inhibiting the enzymatic activity of 1-aminocyclopropane-1-carboxylate oxidase (ACCO) in cut flowers, fruits, and vegetables.

BACKGROUND

A major problem that faces the agriculture industry is timing the ripening of fruits, vegetables and the opening of cut flowers so that such products are not spoiled prior to sale or use. Spoilage accounts for significant losses in agricultural and floriculture markets.

Cut flowers represent a substantial commercial market in the U.S.; the wholesale market is over $400 million. Both growers and retailers of flowers suffer significant losses due to flower spoilage and limited shelf life. Growers typically cut flowers prior to flower opening and store them in a cool environment to delay opening. The flower stems also are typically placed in a preservative solution. Such preservatives generally have a bleach-based biocide, an acid component and a sugar. However, even with such approaches, cut flowers generally can be stored for only short periods of time.

Additionally, there is a tremendous need to improve the shelf life of harvested fruits and vegetables. A significant portion of spoilage of harvested produce is due to accelerated production of ethylene by the harvested plant part. Currently, water spraying, cold storage and sequestering from other ethylene-producing produce items are methods used to control ripening of fruits and vegetables after harvest. Another current method is treatment with ethylene analogs which bind to the ethylene receptor.

Ethylene is an important signaling molecule in plants and influences a variety of processes including plant growth, fruit ripening, and flower development and senescence. Ethylene is synthesized in plants through a series of enzymatic transformations. S-adenosylmethionine (SAM) is converted to 1-aminocyclopropane-1-carboxylic acid (ACC) by ACC synthase. Adams, et al. (1979) Proc. Natl. Acad. Sci. U.S.A. 76:170-174. ACC oxidase then oxidizes ACC to form ethylene. Yang, et al. (1984) Annu. Rev. Plant. Physiol. 35:155-189.

Previous approaches to ethylene biosynthesis in plants have included use of an antisense construct that inhibits expression of a component of the ethylene biosynthesis pathway. Hamilton, et al. (1990) Nature 346:284-287 report the use of an antisense TOM13 (ACC oxidase) gene in transgenic plants. Picton et al. (1993) Plant Journal 3:469-481, report altered fruit ripening and leaf senescence in tomatoes expressing an antisense against the ethylene-forming enzyme. Yet another approach is to transgenically introduce an enzyme that degrades ACC prior to ethylene formation (U.S. Pat. No. 6,271,009). Chemical inhibitors also have been used including those disclosed in U.S. Pat. Nos. 4,957,757 and 4,851,035. Lunkenheimer and Lürssen describe 1-methylamino-cyclopropane-1-carboxylic acid derivatives as plant growth regulators (U.S. Pat. No. 5,041,612). Bregoli, et al., report the use of aminoethoxyvinylglycine (AVG) as an inhibitor of ACC synthase (the prior enzyme in the ethylene pathway in plants) but its utility is limited by the high cost of product and its limited effectiveness. Physiologia Plantarum, Vol. 114 Issue 3, Page 472—March 2002.

There still is a need for improved methods of preventing premature ripening of plants and plant parts while in transit to the market that can be applied to a wide variety of plants.

SUMMARY

Described herein are methods of inhibiting ethylene production in a plant or plant part. Methods described herein include contacting a plant or plant part with an effective amount of an ACC derivative having the formula:

where $R_1$, $R_2$, and $R_7$ may be as follows (a) $R_1$ and $R_7$ are independently selected from H, —OH, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and $R_2$ is —OH, —NH$_2$, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl, —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and R$^4$, R$^5$ and R$^6$ are independently selected from the group consisting of —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl.

(b) $R_1$ and $R_7$ are independently selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; and $C_4$-$C_9$ heterocycloalkyl or $C_4$-$C_9$ heterocycloalkenyl substituted with a group selected from halo, hydroxyl, amino, cyano, and lower alkoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; $C_4$-$C_9$ heterocycloalkyl or $C_4$-$C_9$ heterocycloalkenyl substituted with a group selected from halo, hydroxyl, amino, cyano, and lower alkoxy; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_1$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy; and $R^4$, $R^5$ and $R^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy.

(c) $R_1$ and $R_7$ are independently selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; $C_4$-$C_9$ heterocycloalkyl or $C_4$-$C_9$ heterocycloalkenyl substituted with a group selected from halo, hydroxyl, and methoxy; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; or $C_4$-$C_9$ heterocycloalkyl or $C_4$-$C_9$ heterocycloalkenyl substituted with a group selected from halo, hydroxyl, and methoxy; and $R^4$, $R^5$ and $R^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy.

(d) $R_1$ and $R_7$ are independently selected from H; unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl; and $R_2$ is —OH, —NH$_2$, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; or unsubstituted $C_4$-$C_9$ heterocycloalkyl or $C_4$-$C_9$ heterocycloalkenyl; and R$^4$, R$^5$ and R$^6$ are independently selected from —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl.

(e) $R_7$ is —H; $R_1$ is selected from H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and $R_2$ is —OH, —NH$_2$, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl, —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and R$^4$, R$^5$ and R$^6$ are independently selected from the group consisting of —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl.

(f) $R_7$ is —H; $R_1$ is selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; and $C_4$-$C_9$ heterocycloalkyl or $C_4$-$C_9$ heterocycloalkenyl substituted with a group selected from halo, hydroxyl, amino, cyano, and lower alkoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; $C_4$-$C_9$ heterocycloalkyl or $C_4$-$C_9$ heterocycloalkenyl substituted with a group selected from halo, hydroxyl, amino, cyano, and lower alkoxy; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy; and R$^4$, R$^5$ and R$^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy.

(g) $R_7$ is —H; $R_1$ is selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; $C_4$-$C_9$ heterocycloalkyl or $C_4$-$C_9$ heterocycloalkenyl substituted with a group selected from halo, hydroxyl, and methoxy; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where R$^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; or $C_4$-$C_9$ heterocycloalkyl or $C_4$-$C_9$ heterocycloalkenyl substituted with a group selected from halo, hydroxyl, and methoxy; and R$^4$, R$^5$ and R$^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy.

(h) $R_7$ is —H; $R_1$ is selected from H; unsubstituted $C_1$-$C_6$ alkyl or $C_2$-$C_6$ alkenyl; unsubstituted $C_3$-$C_6$ cycloalkyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl; and $R_2$ is —OH, —NH$_2$, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where R$^3$ is —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; or unsubstituted $C_4$-$C_9$ heterocycloalkyl or $C_4$-$C_9$ heterocycloalkenyl; and R$^4$, R$^5$ and R$^6$ are independently selected from —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl.

(i) any of the ACC derivatives described above with the heteroaryl selected from pyrrolyl, imidazolyl, pyrazolyl, isothiazolyl, isoxazoyl, pyridyl, pyrazinyl, pyrimidineyl, furyl, and thienyl.

(j) any of the ACC derivatives described above with the heteroaryl selected from pyrrolyl, pyridyl, and thienyl.

(k) any of the ACC derivatives described above with the heteroaryl pyrrolyl.

(l) any of the ACC derivatives described above with $R_2$ hydroxyl, amino, or lower alkoxy, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group.

(m) any of the ACC derivatives described above with $R_2$ hydroxyl, —NH$_2$, or methoxy, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group.

(n) any of the ACC derivatives described above with $R_7$ being —H and $R_1$ being —H or lower alkyl.

(o) any of the ACC derivatives described above with $R_7$ being —H and $R_1$ being —H or methyl.

(p) $R_7$ is —H; $R_1$ is —H, $C_1$-$C_4$ alkyl; and $R_2$ is —OH, —OR$^3$ or —NR$^4$R$^5$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where R$^3$ is $C_1$-$C_4$ alkyl; and R$^4$ and R$^5$ are independently selected from the group consisting of —H and $C_1$-$C_4$ alkyl.

(q) $R_7$ is —H; $R_1$ is —H or methyl; and $R_2$ is —OH, —NH$_2$ or —OMe, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group.

In another method described herein of inhibiting ethylene production in a plant or plant part, the plant or plant part is contacted with an effective amount of an ACC derivative selected from The ACC derivative may be ACC-$NH_2$ or N-Me-ACC.

As used herein, an alkyl group can be a straight chained or branched alkyl group, and may include one or more cyclic alkyl moieties. As used herein, an aryl group and a heteroaryl group may be single ring or fused ring groups. Heteroaryl groups may contain one or more heteroatoms.

In one method described herein of inhibiting ethylene production in a plant or plant part, the plant or plant part is contacted with an effective amount of an acyclic compound of the general formula $R_8$—C(H, $NH_2$)—$CO_2H$, where $R_8$ may include any of the $R_1$ to $R_7$ groups listed above.

$R_8$—C(H, $NH_2$)—$CO_2H$ is the general formula for an amino acid. Depending on the $R_5$ group chosen, the resulting compound may be one of the standard 20 amino acids found naturally; it may be a non-naturally occurring amino acid or it may be a modified amino acid. Non-naturally occurring amino acids are generally synthesized chemically. Naturally occurring amino acids may be purified from natural sources such as plants, fungi, bacteria, or yeast, or they may be synthesized chemically.

In yet another method described herein of inhibiting ethylene production in a plant or plant part, the plant or plant part is contacted with an effective amount of an acyclic compound of the formula $R_8$—C(H, $NH_2$)—$CO_2H$ selected from α-aminoisobutyric acid (AIB), D-alanine, and glycine.

In one method described herein, the plant or plant part in which ethylene production is inhibited may be but is not limited to a fruit, a vegetable, a leaf, a branch, a flower, a root or a stem.

In one method described herein, the ACC derivative or acyclic compound is in a solution. In one method the solution is an aqueous solution. In one method described herein, the solution is sprayed on the plant or plant part. In another method described herein, the plant or plant part is immersed or partially immersed in the solution. In another method described herein, the solution is converted to a fog and then applied. In another method described herein, the solution is vaporized and then applied.

In one method described herein, ethylene production is inhibited in apples, pears, stone fruits, avocado, citrus, berries, tomatoes, cherry tomatoes, bananas, cucurbits or grapes. Other plant or plant parts in which ethylene production may be inhibited include but are not limited to hard/soft fruits, vegetables, antisprouting, yellowing of green beans, lettuce, spinach, leafy vegetables, and broccoli. In one method described herein, the plant or plant part is treated before harvesting. In another method described herein, the plant or plant part is treated after harvesting.

Also described herein is a method of delaying the opening of a cut flower. In one such method a cut flower is contacted with a compound having the following structure:

where $R_1$, $R_2$, and $R_7$ are as described above.

In one method of delaying the opening of a cut flower, the ACC derivative is selected from In another such method, a cut flower is contacted with an acyclic compound of the general formula $R_8$—C(H, $NH_2$)—$CO_2H$, where $R_8$ is as described above.

In one method of delaying the opening of a cut flower, an acyclic compound selected from α-aminoisobutyric acid (AIB), D-alanine, and glycine is used.

In one method of delaying the opening of a cut flower the stem end of the cut flower is immersed in an aqueous solution of the ACC derivative or acyclic compound.

Also described herein is a kit for preserving a flower. The kit contains an ACC derivative having the structure:

where $R_1$, $R_2$, and $R_7$ are as described above.

In one kit, the ACC derivative is selected from

Another kit can contain an acyclic compound of the general formula $R_8$—C(H, $NH_2$)—$CO_2H$, where $R_8$ is as described above.

In one kit, an acyclic compound selected from α-aminoisobutyric acid (AIB), D-alanine, and glycine is used.

The kit may be useful both preharvest and postharvest. In one kit described herein, the kit further includes a floral preservative. In one kit described herein, the floral preservative includes one or more of a biocide, an acid, and a sugar. Acids that may be used include but are not limited to acetic acid, hydrochloric acid, sulfuric acid, citric acid or acetylsalicylic acid.

Biocides that may be used include but are not limited to sodium hypochlorite. Sugars that may be used include but are not limited to dextrose. In one kit described herein, the ACC derivative or acyclic compound and the floral preservative are a solid formulation or an aqueous solution.

The kit may be useful in combination treatments with other ethylene inhibitors.

Also described herein is a method of delaying the ripening of a fruit or vegetable by contacting the fruit or vegetable with an effective amount of an ACC derivative having the formula:

where $R_1$, $R_2$, and $R_7$ are as described above.

In another method of delaying the ripening of a fruit or vegetable, the ACC derivative is selected from Another method of delaying the ripening of a fruit or vegetable utilizes an acyclic compound of the general formula $R_8-C(H, NH_2)-CO_2H$, where $R_8$ is as described above.

In another method of delaying the ripening of a fruit or vegetable, an acyclic compound selected from α-aminoisobutyric acid (AIB), D-alanine, and glycine is used.

In one method described herein, the fruit or vegetable for which ripening is delayed is selected from apples, pears, stone fruits, avocado, citrus, berries, tomatoes, cherry tomatoes, bananas, cucurbits or grapes. In one method, the fruit or vegetable is treated preharvest. In one method, the fruit or vegetable is treated post harvest.

DETAILED DESCRIPTION 1-aminocyclopropane-1-carboxylic acid Oxidase (ACCO)

Figure 1:
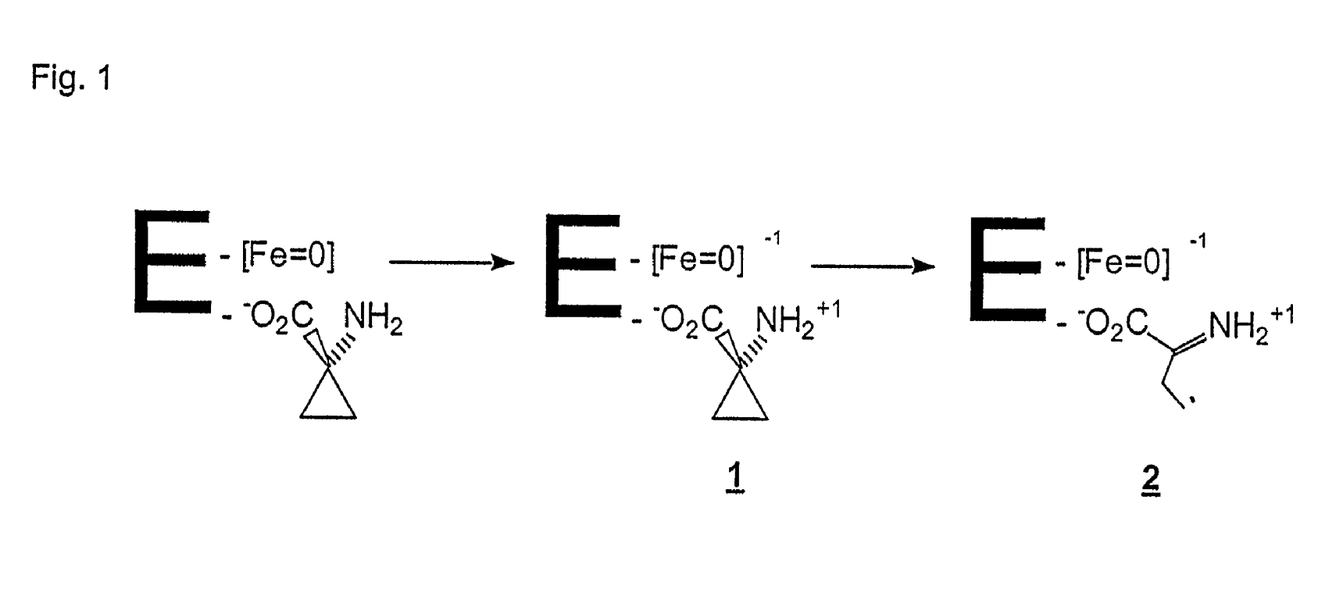
FIG. 1 shows the postulated initiation of the reaction catalyzed by ACCO. As indicated, an activated iron-oxo species abstracts an electron from the amine of a substrate to form a radical cation. This is followed by a structural rearrangement of ACC that ultimately leads to ethylene.
Figure 2:
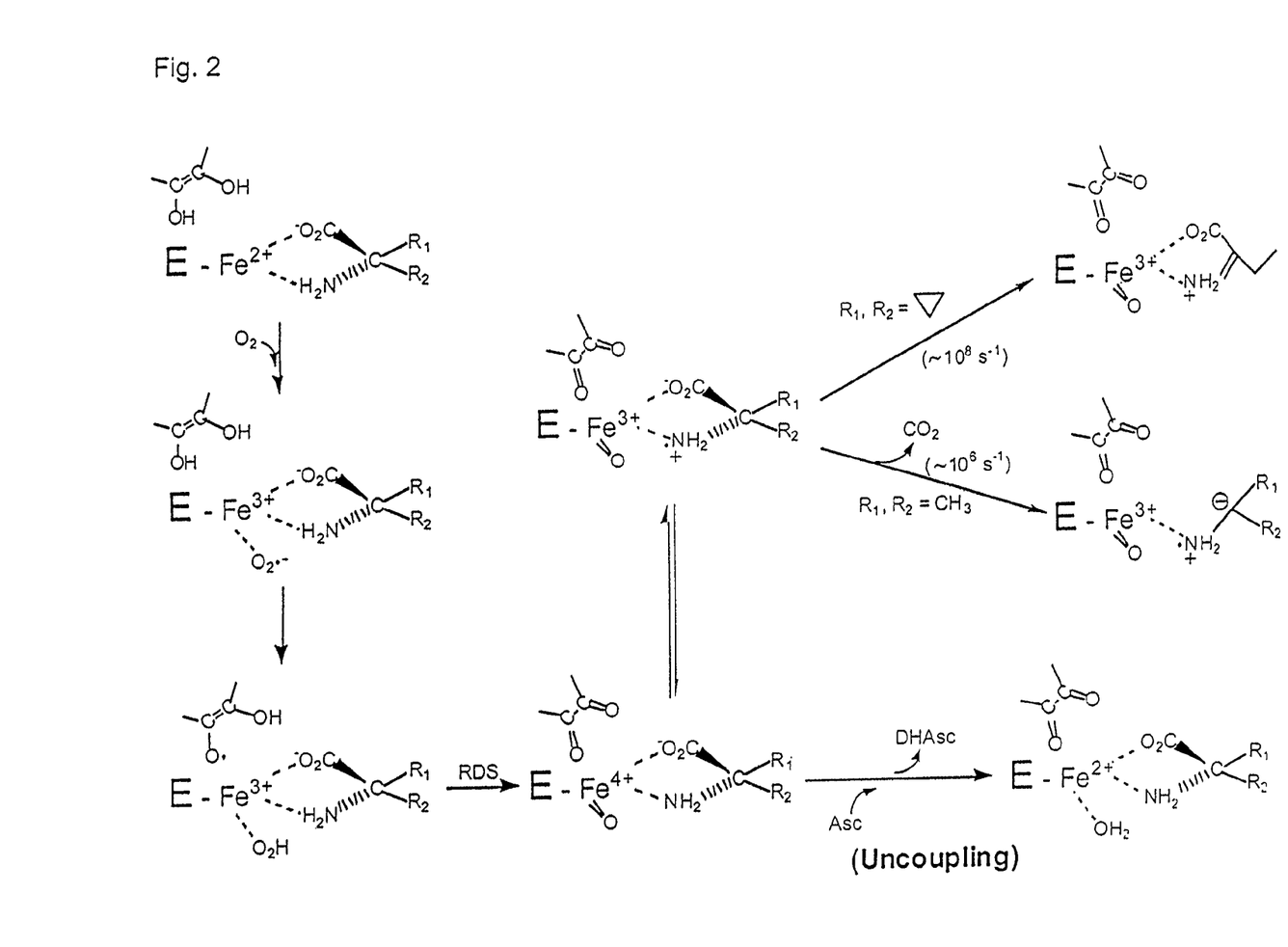
FIG. 2 shows the full postulated mechanism for ACCO. First, substrate binds to the iron, which initiates $O_2$ bending and activation. Subsequently, substrate is oxidized by one electron leading to breakdown of the initial structure. Alternatively, ascorbate (ASC) can enter and reduce the activated iron center. This produces the uncoupled reaction, i.e., $O_2$ uptake without ethylene production.
Figure 3:
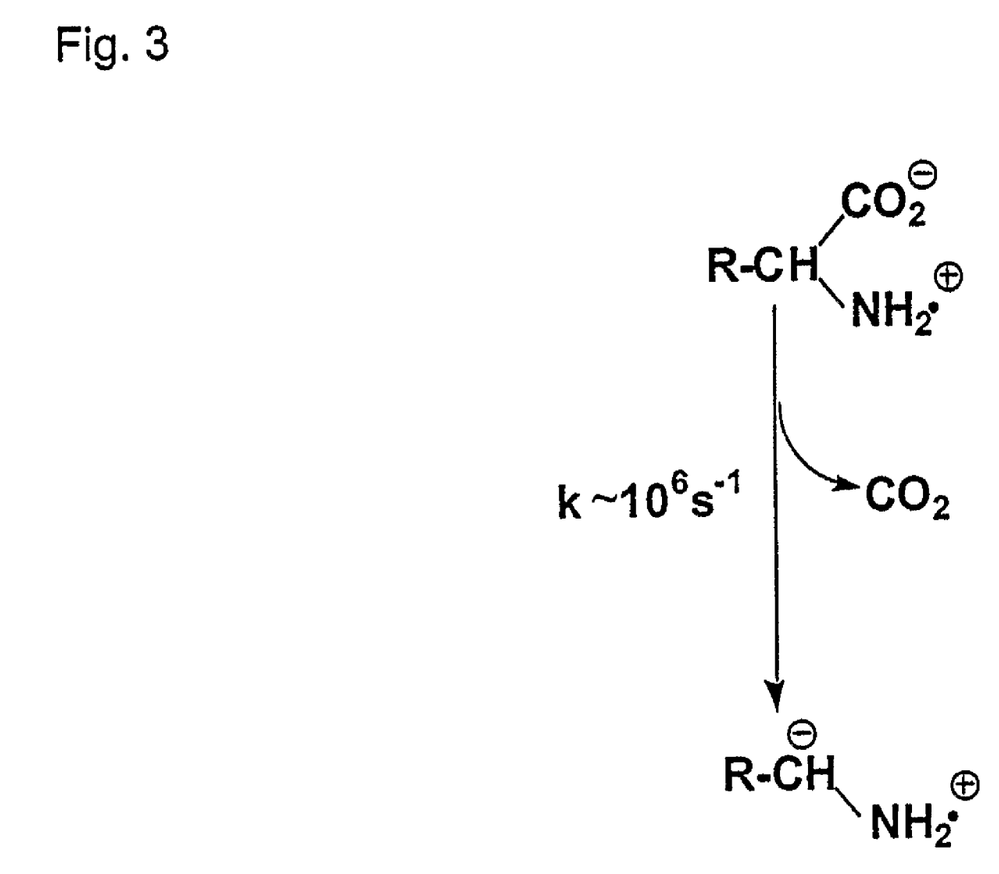
FIG. 3 shows that, for some substrates, the initial one electron oxidation of the amine can lead to decarboxylation.

1-aminocyclopropane-1-carboxylic acid oxidase (ACCO) is a member of the non-heme iron enzyme family which is characterized by a 2-histidine-1 carboxylic acid iron-binding motif. ACCO catalyses the last step in the ethylene biosynthetic pathway: the two electron oxidation of 1-aminocyclopropane-1-carboxylic acid (ACC) to ethylene, carbon dioxide, and cyanide. That reaction requires the simultaneous reduction of molecular oxygen to two equivalents of water and the oxidation of ascorbate to dehydroascorbate.

ACCO Inhibitors

Described herein are ACCO inhibitors of the formula:

(I)

where $R_1$, $R_2$, and $R_7$ may be as follows (a) $R_1$ and $R_7$ are independently selected from H, —OH, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and $R_2$ is —OH, —NH$_2$, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl, —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where $R^3$ is —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and R$^4$, R$^5$ and R$^6$ are independently selected from the group consisting of —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl.

(b) $R_1$ and $R_7$ are independently selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; and $C_4$-$C_9$ heterocycloalkyl or $C_4$-$C_9$ heterocycloalkenyl substituted with a group selected from halo, hydroxyl, amino, cyano, and lower alkoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; $C_4$-$C_9$ heterocycloalkyl or $C_4$-$C_9$ heterocycloalkenyl substituted with a group selected from halo, hydroxyl, amino, cyano, and lower alkoxy; —$OR^3$, —$NR^4R^5$, or —$SR^6$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy; and $R^4$, $R^5$ and $R^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy.

(c) $R_1$ and $R_7$ are independently selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy; and $R_2$ is —OH, —$NH_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; $C_4$-$C_9$ heterocycloalkyl or $C_4$-$C_9$ heterocycloalkenyl substituted with a group selected from halo, hydroxyl, and methoxy; —$OR^3$, —$NR^4R^5$, or —$SR^6$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; or $C_4$-$C_9$ heterocycloalkyl or $C_4$-$C_9$ heterocycloalkenyl substituted with a group selected from halo, hydroxyl, and methoxy; and $R^4$, $R^5$ and $R^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy.

(d) $R_1$ and $R_7$ are independently selected from H; unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl; and $R_2$ is —OH, —$NH_2$, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; —$OR^3$, —$NR^4R^5$, or —$SR^6$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; or unsubstituted $C_4$-$C_9$ heterocycloalkyl or $C_4$-$C_9$ heterocycloalkenyl; and $R^4$, $R^5$ and $R^6$ are independently selected from —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl.

(e) $R_7$ is —H; $R_1$ is selected from H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and $R_2$ is —OH, —NH$_2$, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl, —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where R$^3$ is —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl; and R$^4$, R$^5$ and R$^6$ are independently selected from the group consisting of —H, substituted or unsubstituted $C_1$-$C_6$ alkyl or $C_2$-$C_6$ alkenyl, substituted or unsubstituted $C_3$-$C_8$ cycloalkyl or $C_3$-$C_8$ cycloalkenyl, substituted or unsubstituted $C_6$-$C_{10}$ aryl, substituted or unsubstituted $C_6$-$C_{14}$ aralkyl or $C_6$-$C_{14}$ aralkenyl, substituted or unsubstituted $C_4$-$C_9$ heteroaryl, or substituted or unsubstituted $C_4$-$C_9$ heterocycloalkyl or $C_4$-$C_9$ heterocycloalkenyl.

(f) $R_7$ is —H; $R_1$ is selected from H; unsubstituted $C_2$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; and $C_4$-$C_9$ heterocycloalkyl or $C_4$-$C_9$ heterocycloalkenyl substituted with a group selected from halo, hydroxyl, amino, cyano, and lower alkoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; $C_4$-$C_9$ heterocycloalkyl or $C_4$-$C_9$ heterocycloalkenyl substituted with a group selected from halo, hydroxyl, amino, cyano, and lower alkoxy; —OR$^3$, —NR$^4$R$^5$, or —SR$^6$, except $R_2$ is not —OH, substituted alkoxy, alkenyloxy, alkinyloxy, cycloalkoxy, —NH$_2$, alkylamino, dialkylamino when $R_1$ is H or an acyl group and $R_7$ is methyl or $R_1$ is methyl and $R_7$ is H or an acyl group; where R$^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy; and R$^4$, R$^5$ and R$^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, amino, cyano, and lower alkoxy; $C_3$-$C_8$ cycloalkyl or $C_3$-$C_8$ cycloalkenyl substituted with a group selected from halo, hydroxyl, amino, cyano, and lower alkoxy; $C_6$-$C_{10}$ aryl substituted with a group selected from halo, hydroxyl, amino, cyano, and lower alkoxy; $C_6$-$C_{14}$ aralkyl or $C_6$-$C_{14}$ aralkenyl substituted with a group selected from halo, hydroxyl, amino, cyano, and lower alkoxy; $C_4$-$C_9$ heteroaryl substituted with a group selected from halo, hydroxyl, amino, cyano, and lower alkoxy; or $C_4$-$C_9$ heterocycloalkyl or $C_4$-$C_9$ heterocycloalkenyl substituted with a group selected from halo, hydroxyl, amino, cyano, and lower alkoxy.

(g) $R_7$ is —H; $R_1$ is selected from H; unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy; and $R_2$ is —OH, —NH$_2$, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; $C_4$-$C_9$ heterocycloalkyl or $C_4$-$C_9$ heterocycloalkenyl substituted with a group selected from halo, hydroxyl, and methoxy; —$OR^3$, —$NR^4R^5$, or —$SR^6$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; or $C_4$-$C_9$ heterocycloalkyl or $C_4$-$C_9$ heterocycloalkenyl substituted with a group selected from halo, hydroxyl, and methoxy; and $R^4$, $R^5$ and $R^6$ are independently selected from —H, unsubstituted $C_1$-$C_6$ alkyl or $C_2$-$C_6$ alkenyl; unsubstituted $C_3$-$C_8$ cycloalkyl or $C_3$-$C_8$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; $C_1$-$C_6$ alkyl or $C_2$-$C_6$ alkenyl substituted with a group selected from halo, hydroxyl, and methoxy; $C_3$-$C_8$ cycloalkyl or $C_3$-$C_8$ cycloalkenyl substituted with a group selected from halo, hydroxyl, and methoxy; $C_6$-$C_{10}$ aryl substituted with a group selected from halo, hydroxyl, and methoxy; $C_6$-$C_{14}$ aralkyl or $C_6$-$C_{14}$ aralkenyl substituted with a group selected from halo, hydroxyl, and methoxy; $C_4$-$C_9$ heteroaryl substituted with a group selected from halo, hydroxyl, and methoxy; and $C_4$-$C_9$ heterocycloalkyl or $C_4$-$C_9$ heterocycloalkenyl substituted with a group selected from halo, hydroxyl, and methoxy.

(h) $R_7$ is —H; $R_1$ is selected from H; unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl; and $R_2$ is —OH, —$NH_2$, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; unsubstituted $C_4$-$C_9$ heterocycloalkyl or $C_4$-$C_9$ heterocycloalkenyl; —$OR^3$, —$NR^4R^5$, or —$SR^6$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is —H, unsubstituted $C_1$-$C_6$ alkyl or $C_2$-$C_6$ alkenyl; unsubstituted $C_3$-$C_6$ cycloalkyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; or unsubstituted $C_4$-$C_9$ heterocycloalkyl or $C_4$-$C_9$ heterocycloalkenyl; and $R^4$, $R^5$ and $R^6$ are independently selected from —H, unsubstituted $C_1$-$C_6$ alkyl or $C_2$-$C_6$ alkenyl; unsubstituted $C_3$-$C_6$ cycloalkyl or $C_3$-$C_6$ cycloalkenyl; unsubstituted $C_6$-$C_{10}$ aryl; unsubstituted $C_6$-$C_{14}$ aralkyl or $C_6$-$C_{14}$ aralkenyl; unsubstituted $C_4$-$C_9$ heteroaryl; and unsubstituted $C_4$-$C_9$ heterocycloalkyl or $C_4$-$C_9$ heterocycloalkenyl.

(i) any of the ACC derivatives described above with the heteroaryl selected from pyrrolyl, imidazolyl, pyrazolyl, isothiazolyl, isoxazoyl, pyridyl, pyrazinyl, pyrimidineyl, furyl, and thienyl.

(j) any of the ACC derivatives described above with the heteroaryl selected from pyrrolyl, pyridyl, and thienyl.

(k) any of the ACC derivatives described above with the heteroaryl pyrrolyl.

(l) any of the ACC derivatives described above with $R_2$ hydroxyl, amino, or lower alkoxy, except when $R_1$ is H or an acyl group and $R_7$ is methyl or $R_1$ is methyl and $R_7$ is H or an acyl group.

(m) any of the ACC derivatives described above with $R_2$ hydroxyl, —$NH_2$, or methoxy, except when $R_1$ is H or an acyl group and $R_7$ is methyl or $R_1$ is methyl and $R_7$ is H or an acyl group.

(n) any of the ACC derivatives described above with $R_7$ being —H and $R_1$ being —H or lower alkyl.

(o) any of the ACC derivatives described above with $R_7$ being —H and $R_1$ being —H or methyl.

(p) $R_7$ is —H; $R_1$ is —H, $C_1$-$C_4$ alkyl; and $R_2$ is —OH, —$OR^3$ or —$NR^4R^5$, except $R_2$ is not —OH, substituted alkoxy, alkenyloxy, alkinyloxy, cycloalkoxy, —$NH_2$, alkylamino, dialkylamino when $R_1$ is H or an acyl group and $R_7$ is methyl or $R_1$ is methyl and $R_7$ is H or an acyl group; where $R^3$ is $C_1$-$C_4$ alkyl; and $R^4$ and $R^5$ are independently selected from the group consisting of —H and $C_1$-$C_4$ alkyl.

(q) $R_7$ is —H; $R_1$ is —H or methyl; and $R_2$ is —OH, —$NH_2$ or —OMe, except when $R_1$ is H or an acyl group and $R_7$ is methyl or $R_1$ is methyl and $R_7$ is H or an acyl group.

Also described herein are ACCO inhibitors having the formula (II)

Further described are ACCO inhibitors which are acyclic compounds having the general formula $R_8$—C(H, $NH_2$)—$CO_2H$, where $R_8$ may include any of the $R_1$ to $R_7$ groups listed above.

Further described herein are ACCO inhibitors which are acyclic compounds selected from α-aminoisobutyric acid (AIB), D-alanine, and glycine.

ACCO inhibitors that may be used in the kits and methods described herein can be identified by assessing a potential ACC inhibitor's ability to inhibit an ACC oxidase in vitro. Using three dimensional structural information of an ACC oxidase enzyme, improved inhibitors can be designed. Such techniques for computer-aided inhibitor design are known to one of skill in the art. Based on the known coordinating of ACC to the iron in the enzyme, substitutions can be designed that will be sterically tolerated. Charged groups also may be introduced to facilitate charge-charge interactions between the inhibitor and the enzyme. One of skill in the art also will recognize that a large number of ACCO inhibitors can be generated using combinatorial chemistry methods. The compounds, either pooled or individually, can be tested for the ability to inhibit ACCO in vitro. An ACCO inhibitor can act by a number of mechanisms.

In one mechanism, the ACCO inhibitor acts as a reversible competitive or non-competitive inhibitor of the enzyme. In reversible competitive inhibition, the inhibitor binds to the same binding site (the active site) as the enzyme's natural substrate. By competing for binding, the action of the enzyme toward its natural substrate is inhibited. The inhibitor molecule may undergo reaction while bound to the enzyme or may not, depending on the structure of the inhibitor molecule. In either case, the interaction is reversible as the inhibitor (modified or not) is released from the enzyme, allowing the enzyme to undergo catalysis or be subject to further inhibition depending on whether the natural substrate or an inhibitor molecule binds in the active site. Competitive inhibition is characterized by the ability to overcome inhibition by raising the concentration of the natural substrate, while maintaining the concentration of the inhibitor constant.

Another form of inhibition is non-competitive inhibition. In non-competitive inhibition, the inhibitor binds to a site distinct from the site bound by the natural substrate. Thus, in this type of inhibition, the inhibition can not be overcome by raising the concentration of the natural substrate.

In one method, ACCO inhibitors can be acyclic compounds such as α-aminoisobutyric acid (AIB), D-alanine, and glycine. These acyclic compounds compete with ACC for binding to the ACCO active site. Upon binding, these compounds undergo a simple decarboxylation reaction to release compounds such as acetone, acetaldehyde, and $CO_2$. By binding to the ACCO active site, these acyclic compounds are able to inhibit the ability of ACCO to generate ethylene from its natural substrate, ACC. Because α-aminoisobutyric acid (AIB), D-alanine, and glycine are relatively non-toxic to plants, these compounds can be applied to plants and plant parts at the higher concentrations necessary to compensate for the less effective binding of these compounds to the ACCO enzyme, as indicated by their higher Km values. (See Table 1 below.)

Many of the acyclic compounds are standard or modified amino acids which should be permeable to plant tissues and thus be accessible to the ACCO enzyme. Other variants of the general formula $R_8$—C(H, $NH_2$)—$CO_2H$ will also be useful in the practice of this invention, depending on factors such as cell permeability and any potential side effects.

In another mechanism, an ACCO inhibitor uncouples oxygen activation from inhibitor/substrate activation. In another mechanism, the ACCO inhibitor binds to the enzyme and covalently modifies the enzyme, acting as a suicide inhibitor.

The invention includes the compounds described herein or incorporated by reference herein, including any and all stereoisomers, salts, hydrates and solvates of the compounds described herein or incorporated by reference herein. The invention also includes the compounds described herein or incorporated by reference herein in their non-salt, non-hydrate/non-solvate form. Thus, while some compounds disclosed herein are depicted as salts, it is to be understood that the disclosure embraces all other salts, hydrates, and solvates of the compounds depicted therein, as well as the non-salt, non-hydrate/non-solvate form of the compound. Particularly preferred are biologically acceptable salts. Biologically acceptable salts are those salts which retain the biological activity of the free compounds and which are not biologically or otherwise undesirable. The desired salt of a basic compound may be prepared by methods known to those of skill in the art by treating the compound with an acid; such a salt can be the product of a reaction producing the compound. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base; such a salt can be the product of a reaction producing the compound. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dicyclohexylamine, dibenzylamine, N-ethylpiperidine, N,N'-dibenzylethylenediamine, and triethylamine salts. Salts of acidic compounds with amino acids, such as lysine salts, can also be prepared. Examples of solvates include, but are not limited to, hydrates, hemihydrates (½$H_2O$), dihydrates, trihydrates, and alcoholates such as methanolates and ethanolates.

The invention also includes all polymorphs, crystalline forms, and non-crystalline forms of the compounds disclosed herein.

The invention also includes all stereoisomers of the compounds disclosed herein, including diastereomers and enantiomers in isolated form, as well as mixtures of stereoisomers in any proportion, including, but not limited to, racemic mixtures. Unless stereochemistry is explicitly indicated in a structure, the structure is intended to embrace all possible stereoisomers of the compound depicted.

Cut Flowers

Described herein is a method by which a cut flower can be preserved or its opening prevented or delayed by contacting the cut flower with a solution of an ACCO inhibitor as described herein. In one method, the flower and supporting stem are cut and the cut end of the stem is placed in an aqueous solution of an ACCO inhibitor. The solution can have one or more other floral preservatives in addition to the ACCO inhibitor. When opening of the flower is desired, the flower can be placed in water that does not contain the ACCO inhibitor, or that contains a lower concentration of the ACCO inhibitor. The ACCO inhibitors also can be used to preserve a flower that has already opened. For example, already opened flowers can be placed in water containing an ACCO inhibitor to delay senescence (e.g., wilting or dying) of the flower. The ACCO inhibitors useful for delaying senescence or preventing flower opening are present at concentrations sufficient to have the desired effect. Such effective concentrations can be determined by routine experimentation either on plants, or based on the affinity of the inhibitor for ACCO. For example, where the inhibitor is also a substrate for ACCO, the inhibitor is present generally in a concentration of at least about one-tenth of the Km value of the inhibitor/substrate for the enzyme. In one method described herein, the inhibitor is present in a greater concentration than the Km value for the substrate/inhibitor.

Because the ethylene biosynthesis pathway is conserved across various plants, the methods described herein can generally be used with any plant or flower. Examples of commercially relevant cut flowers include, but are not limited to: alstroemeria, carnations, chrysanthemums, delphinium, gerbera daisy, gladioli, iris, lilies, lisianthus, orchids, roses, snapdragons, and tulips.

Floral Preservatives

A number of floral preservatives are known to one of skill in the art. Floral preservatives include, for example, sugars, for example dextrose, sucrose and the like. Flower preservatives also include acids (and salts thereof), for example, citric acid, acetylsalicylic acid, hydrochloric acid, sulfuric acid, and the like. Floral preservatives also include biocides capable of inhibiting bacterial or fungal growth on the cut flower stem. The biocide used may be sodium hypochlorite. Floral preservatives used may include a combination of one or more of the above acid, biocide and sugar.

Kits

An ACCO inhibitor can be packaged in a kit with a floral preservative. The kit can include the ACCO inhibitor and floral preservative as a solid (e.g. an amorphous or crystalline powder) suitable for making a solution having a concentration suitable for the storage of cut flowers.

A kit also can be sold as a concentrated solution which can be diluted to give the effective solution. In one kit described herein, the floral preservative includes at least one of a biocide, an acid and a sugar. In another kit described herein, the kit contains the ACCO inhibitor and at least two of a biocide, an acid and a sugar. In another kit described herein, the kit contains the ACCO inhibitor and a biocide, an acid and a sugar.

Fruits and Vegetables

When used with an edible fruit or vegetable, the fruit or vegetable is either submerged in or sprayed with a solution of an ACCO inhibitor. For such usage, in one method described herein the inhibitor is tested for any toxicity, such that any ACCO inhibitor residue present on such fruits or vegetable will not pose a health hazard. In one method described herein, a toxic ACCO inhibitor may be used which may be later removed. Suitable fruits and vegetables for treatment include, but are not limited to, members of the apple family, the pear family, stone fruits, avocado, citrus, berries, tomatoes, cherry tomatoes, bananas, cucurbits, grapes and others.

The following non-limiting examples were carried out demonstrating the methods described herein.

Synthesis of ACCO inhibitor

The ACC derivatives described herein may be prepared by a variety of methods as is known in the art. One example of methods that may be used is described in US patent application 2001/0041700, the contents of which is incorporated herein by reference in its entirety. The ACC derivatives described herein may be prepared as described in the examples below.

EXAMPLES

Example 1

Materials

All reagents were purchased from Sigma or Aldrich unless otherwise indicated. All radiochemicals were purchased from American Radiolabeled Chemicals except for [1-$^{14}$C]-Gly, which was purchased from ICN Biomedicals. Purity of radiolabeled compounds was determined by thin layer chromatography. A known amount of each compound was diluted with a nonradiolabeled standard and spotted on a silica plate. Solvent: n-butanol: acetic acid:water (4:1:1). The compound was localized by staining with either iodine or ninhydrin. Spots were scrapped off into a scintillation vial and the radioactivity determined. Purity was determined by measuring the amount of radioactivity that ran with the known non-radiolabeled standard as compared to that of an undeveloped plate. All radiolabeled compounds were >98% pure except [carboxyl-$^{14}$C]-ACC, which was ~20% pure.

Overexpression and Purification of ACCO.

ACCO from *Lycopersicon esculentum* (ACO1) was produced in *Escherichia coli* strain BL21 (DE3)pLysS and purified by a two-column purification procedure as previously described (Thrower, J. S. et al., 2001).

Synthesis of N-BOC-ACC

N-BOC-ACC was synthesized by (1) adding ACC to water dioxane (1:1) mixture, (2) adding TEA to the mixture, (3) stirring until all components dissolved, (4) adding BOC-ON to the mixture, and (5) stirring the mixture overnight.

Synthesis of N-Me-ACC and N-[$^{14}$C-methyl]-ACC

MeACC was synthesized as follows. Anal. Calculated for $C_5H_9NO_2$: 115.06318. Found: 115.06333. N-[$^{14}$C-methyl]-ACC was synthesized by the same procedure except using [$^{14}$C]—$CH_3I$ diluted with nonradiolabeled $CH_3I$ to a specific activity of 10 µCi/mmol. Purity of N-[$^{14}$C-methyl]-ACC was determined by TLC as described above, and was found to be >98% pure.

Synthesis of $ACCNH_2$

N-Boc-ACC was prepared as described above. N-Boc-ACC (0.2 g, 1 mmol) and HOBT (1-hydroxybenzotriazole hydrate) (0.135 g, 1 mmol) were added to anhydrous DMF (dimethylformamide) (5 mL) and stirred on ice until dissolved. EDC (1-(3-dimethylaminopropyl)-3-ethylcarbodiimide hydrochloride) (0.192 g, 1 mmol) was added to the DMF solution and stirred on ice for 3 h. Anhydrous 7 N $NH_3$ in methanol (1.5 mL, ~10 mmol) and TEA (triethylamine) (0.31 mL, ~2 mmol) were added to the cool mixture and stirred on ice for 1 h followed by overnight at ambient temperature. The DMF was evaporated and the resulting oil was resuspended in 20 mL EtOAc and washed with saturated NaHO3, 0.5 M citric acid, and brine. The organic layer was dried and evaporated to yield a yellow residue. TFA (trifluoroacetic acid) (0.5 mL) was added to the residue, stirred at ambient temperature for 2 h, and evaporated. 1 M HCl (5 mL) was added, stirred briefly, and evaporated to yield a yellow oil. The oil was resuspended in 10 mL ether. The precipitated $ACCNH_2$ was filtered and dried to yield 134 mg (30%) of white solid.

Initial Velocity Assays

Initial velocities were measured by the rate of oxygen consumption at 25° C., pH 7.2, using a YSI model 5300 biological oxygen monitor as previously described (Thrower 2001) with minor modifications. Standard reaction mixture (1 ml) contained 100 mM MOPS, pH 7.2, 20 mM NaHCO3, 100 mM NaCl, 20 mM sodium ascorbate, 0.1 mg/ml BSA, and ACC or substrate analog at various concentrations. Oxygen concentrations were kept at atmospheric concentration and determined using the oxygen monitor that was calibrated with air saturated water (258 µM oxygen at 25° C.). Reactions were initiated with 2 µL ACCO reconstituted with equimolar $Fe(NH_4)_2(SO_4)_2$. The concentration of ACCO is as indicated in figure legends. Data from initial velocity experiments with varying substrate concentrations were fitted to the Michaelis-Menton equation using the program Kalideograph.

TABLE 1

Kinetic Parameters for ACC Oxidase with Various Substrate Analogs[a]

| Substrate | $V_{max}$ (min$^{-1}$) | $K_m$ (mm) | Substrate | $V_{max}$ (min$^{-1}$) | $K_m$ (mm) |
|---|---|---|---|---|---|
| ACC | 36.4 ± 1.4 | 0.099 ± 0.018 | | | |
| N-Me-ACC | 12.2 ± 0.5 | 0.107 ± 0.021 | AIB | 22.1 ± 1.6 | 0.92 ± 0.29 |
| ACC-NH$_2$ | 11.3 ± 0.6 | 0.214 ± 0.047 | D-Alanine | 29.8 ± 0.9 | 4.42 ± 0.49 |
| ACC-OMe | 27.3 ± 1.7 | 2.76 ± 0.55 | Glycine | 9.5 ± 0.6 | 1.0 ± 0.4 |

[a]Kinetic parameters were determined by measuring initial velocities at various concentrations of substrate while maintaining ascorbate and oxygen at a constant concentration.
[Ascorbate] = 30 mM, [O$_2$] = 258 μM, and [CO$_2$/bicarbonate] = 20 mM.

As can be seen from the above data, the $K_m$ values for MeACC and ACCNH$_2$ were not significantly altered compared to ACC, while the $K_m$ for ACC-OMe was increased ~28-fold. Spectroscopic studies have identified that both the amine and carboxylate groups of ACC are ligands to the active site Fe(II) (Rocklin et al., 1999). It is possible that both MeACC and ACCNH$_2$ would still form a bidentate ligand to the Fe(II) center, and thus result in an equal or greater affinity for the enzyme. Likewise, ACC-OMe may be capable of forming a bidentate ligand to the Fe(II) center, but one possibility for the observed decreased affinity is that it does not form a bidentate ligand. In one method for identifying ACCO inhibitors for us in the methods described herein, the ACCO inhibitor will be able to form such a bidentate interaction with the Fe(II) center.

As can also be determined from Table 1, the $K_m$ of the acyclic compounds, α-aminoisobutyric acid (AIB), D-alanine, and glycine, are increased by factors of 9.3, 44.7, and 10.1, respectively, when compared with the natural substrate, ACC. The $V_{max}$ values for the acyclic compounds show a less dramatic difference than that observed with ACC as the substrate.

The dependence of the initial velocity of oxygen consumption by ACCO:Fe(II) on the concentration of ACC or several substrate analogs was determined (Table 1). Either cyclic substrate analogs (including inhibitor Me-ACC, ACC-NH$_2$, or ACC-OMe) or acyclic substrate analogs (AIB, D-Ala, or Gly) were used. The presence of any one of the substrate analogs resulted in the immediate increase of O$_2$ consumption by ACCO:Fe(II) and, as expected, the dependence of the initial rate on substrate concentration followed Michaelis-Menton kinetics. Ascorbate and oxygen concentrations were kept constant at 30 mM and ~258 μM, respectively. These concentrations were previously shown to be saturating when ACC was the substrate (Thrower et al., 2001), and were assumed to be at saturating concentrations when substrates other than ACC were used. Additionally, measurement of the $K_m$ values for O$_2$ or ascorbate in the presence of saturating concentrations of MeACC resulted in similar $K_m$ values compared to those when ACC was the substrate. This result indicated that slight perturbations in the substrate structure did not affect the Km values of O$_2$ or ascorbate for the enzyme.

Ethylene and CO$_2$ Trapping Assays

For detection of CO$_2$, trace radiolabeled compound was used as appropriate. A small vial containing the reaction mixture minus enzyme was placed along side of another small vial containing the ethylene or CO$_2$ trap. Both vials were placed in a large vial, which was capped with a septum. ACCO:Fe(II) was introduced into the reaction vial with a syringe and both the reaction vial and trap vial were stirred for 1 h. For [$^{14}$C]—CO$_2$ trapping, a 1 mL solution of freshly prepared 10 M NaOH was used as the trapping agent. At the end of the reaction, the trap was removed and added to 15 mL scintillation fluid (Hionic-Fluor, Perkin Elmer) and radioactivity determined by scintillation counting. For ethylene, a 500 mL solution of Br$_2$ in CCl$_4$ was used as the trap. A small amount of 2,5-dibromohexane was added to the trap as an internal standard. At the completion of the reaction, a small excess of 2,3-dimethyl-2-butene was added to the trap to quench unreacted Br$_2$, and the trap was analyzed by GC-MS. Dibromoethane purchased from Aldrich was used as a standard.

Stoichiometry of O$_2$ Consumption to CO$_2$ Production

Oxygen consumption was measured using a YSI model 5300 biological oxygen monitor as described above. Reactions contained D-[1-$^{14}$C]-Ala, [carboxyl-$^{14}$C]-ACC, α-[1-$^{14}$C]-AIB, or [1-$^{14}$C]-Gly in trace amounts. Substrates were kept at saturating concentrations (at least 10-fold above Km), 30 mM ascorbate, and ambient O$_2$ concentrations. Reactions (1 mL) were initiated with a pre-incubated mixture of ACCO:Fe(II) in a 2:1 ratio. This was done to minimize free Fe(II) in solution. Final concentrations were typically 10 μM ACCO and 5 μM Fe(II). Reactions were quenched by addition of 3 μL of 0.1 M 3-[2-Pyridyl]-5,6-diphenyl-1,2,4-triazine-4,4'-disulfonic acid (FERROZINE®) and the O$_2$ consumption rate was allowed to stabilize. The reaction (0.8 mL) was removed with a gas-tight syringe and injected into a small vial containing 0.1 mL 10% HCl that was inside a larger vial containing the CO$_2$ trap (see above). The acidified reaction mixture and the CO$_2$ trap were stirred for 2 h, and radioactivity from [$^{14}$C]—CO$_2$ was determined as described above. Controls measuring the efficiency of the CO$_2$ trap were done by injecting a known amount of [$^{14}$C]—NaHCO$_3$ into the vial containing acid, as above, and measuring the amount of [$^{14}$C]—CO$_2$ recovered. Efficiency of trapping was routinely ~98%.

O$_2$ consumption was measured using an Ocean Optics FOXY fiber optic oxygen sensor, with the fiber optic probe inserted through a syringe into an airtight septum, thus preventing ethylene escape. Substrates were kept at saturating concentrations (at least 10-fold above $K_m$), 30 mM ascorbate, and ambient O$_2$ concentrations. ACCO:Fe(II) (final concentrations 10 μM ACCO and 5 μM Fe(II)) was injected by syringe into a ½ dram vial covered with a septum with no headspace. The reaction was quenched as described above. A 10 mL syringe filled with air was used to transfer the reaction mixture to a 10 mL test tube covered with a septum using a cannula. The test tube was stirred vigorously for at least 4 hours before ethylene analysis. Ethylene was measured by injecting 2 mL of the headspace onto a GC equipped with a RT-Alumina GC column (final sample size was 250 μL). Ethylene was separated using ultrapure helium (grade 5) as the carrier gas at 40° C. detected by flame ionization (FID).

The data were collected and the peak area was determined. Calibration for ethylene was done with Scotty IV mix 3 hydrocarbon standard (Scotty Specialty Gases). The ppm of ethylene was converted to nanomoles of ethylene per unit volume using the ideal gas law. Dilution of ethylene during sampling was taken into account in the calculations.

The results show that ACCO consumes $O_2$ in the presence of either AIB or D-Ala at a rate comparable to that with ACC (Table 1). However, this is not indicative of substrate turnover. There have been several examples of related non-heme iron enzymes that activate $O_2$ without corresponding substrate turnover in what is called an "uncoupled" reaction (Holme et al., 1982, and Liu et al., 2001). In some cases, significant uncoupling even occurs during normal catalysis with the physiological substrate (Holme et al., 1982) and leads to either reversible or irreversible enzyme inactivation (Barlow et al., 1997, and Liu et al., 2001).

The ability of ACCO to turnover ACC or the cyclic substrate analogs (MeACC, ACC-$NH_2$, or ACC-OMe) was determined by the formation of ethylene. Each substrate analog or ACC was incubated for 1 hr with ACCO:Fe(II) in a closed reaction vial containing an ethylene trap that would convert ethylene to dibromoethane. At the end of the reaction time, the ethylene trap was quenched and analyzed for dibromoethane by GC-MS. Reactions with BSA/Fe(II) were used as a control for non-enzymatic ethylene formation. The formation of ethylene was detected in the reaction vials of ACC and all the cyclic analogs in the presence of ACCO:Fe(II). No ethylene was detected in any of the BSA/Fe(II) reactions. The amount of ethylene formed during the reaction time from the cyclic analogs was lower than that from the reaction with ACC (MeACC=14%, ACC$NH_2$=13%, ACC-OMe=79%). If the rates of $O_2$ consumption for the reactions with the different substrates are considered, the $k_{cat}$ for ACC-OMe is approximately 75% of that for ACC, which would be consistent with the amount of ethylene produced during the time course of the reaction. However, ACC$NH_2$ and MeACC had $k_{cat}$ values ~30% slower than the $k_{cat}$ for ACC, but only produced about half the predicted ethylene during the reaction time course. Although the purity of both MeACC and ACC$NH_2$ by elemental analysis was determined >95%, it is possible that a small amount of contaminating ACC could be responsible for the ethylene formed in these reactions. To determine whether ethylene was being formed from the substrate analog and not from contaminating ACC, reactions with each analog were done in the presence of increasing concentration of ACCO:Fe(II). In the case of a small amount of contamination where the ACC would be quickly depleted during the reaction, the result would be a non-linear dependence of ethylene production with increasing ACCO concentration. For ACC and all cyclic analogs, the amount of ethylene production with increasing concentration of ACCO showed a linear dependence, indicating that ethylene production was due to substrate analog turnover rather than ACC contamination.

Example 2

Inhibition of ACCO by N-Me-ACC

Using the following protocol, it was demonstrated that radiolabeled N-methyl-ACC irreversibly labels ACCO in a short period of time. Radiolabeled N-Me-ACC was incubated with ACCO (approximately equal concentrations) in standard reaction conditions. The reaction was quenched using Ferrozine. The solution was placed in a Millipore 10K NMWL Ultrafree®-MC Centrifugal Filter Unit and centrifuged for 15 min. at 14K rpm. The remaining protein (~20 µL) was washed with 3×1 mL of either water, reaction buffer, or 0.1% TFA by repeated centrifugation. The protein was collected and radioactivity determined by scintillation counting in 12 mL EcoLite$^+$ scintillation fluid.

Stoichiometry of $O_2$ Consumed to Product Formed

The extent of uncoupling for ACCO with both cyclic and acyclic substrate analogs was determined by comparing the amount of $O_2$ consumed and product, either ethylene or $CO_2$, formed. All reactions were carried out at saturating substrate and ascorbate concentrations to minimize potential $O_2$ reaction in the absence of substrate. Enzyme was reconstituted with 0.6 equivalents of Fe(II) and kept at high concentration (12-fold higher than Kd) to minimize free Fe(II) in the reaction. $O_2$ measurements were quenched during or just as the linear phase of the reaction began to fall off due to either loss of Fe(II) from the enzyme or possible enzyme inactivation. The results distinguish between amounts of uncoupling.

For cyclic substrate analogs and ACC, the stoichiometry was determined by comparing $O_2$ consumption with ethylene formation by GC-FID. For the acyclic substrate analogs that were shown to release $CO_2$ as a product, as well as ACC, $O_2$ consumption was compared with the formation of [$^{14}$C]—$CO_2$. Ratios of $O_2$ consumption to product formation are shown in Table 3. The stoichiometry of $O_2$ consumed to ethylene produced for ACC was 1.44 and to $CO_2$ produced was 1.18, which is identical to that reported by Dong, et. al (Dong et al., 1992).

All cyclic and acyclic substrates showed some increased level of uncoupling over ACC. However, with the cyclic substrates there was no correlation of the extent of uncoupling and whether the amine (MeACC) or the carboxylate (AC-CNH$_2$ or ACC-OMe) had been perturbed. In the case of the acyclic substrates, a more definite pattern emerged where the extent of uncoupling was affected by the substrate structure. Breaking the cyclic ring but maintaining both methyl groups in AIB resulted in some increased uncoupling over the ACC reaction (1.7 for AIB versus 1.2 for ACC). However, each successive removal of a methyl group from AIB to Ala and then to Gly resulted in a further increase in the extent of uncoupling, with Gly having the most extreme affect of only one of about every 21 reactions with $O_2$ resulting in Gly turnover.

TABLE 2

Stoichiometry of Oxygen Reduction Catalyzed by ACC Oxidase with Various Substrates

| | Ratio $O_2$ consumed to product formed | | |
|---|---|---|---|
| Substrate | $O_2$:$CO_2$ | $O_2$:ethylene | Products detected |
| ACC | 1.18 ± 0.17 | 1.44 ± 0.22 | Ethylene, $CO_2$ |
| N-Me-ACC | — | 3.17 ± 0.86 | Ethylene |
| ACC-$NH_2$ | — | 4.40 ± 1.56 | Ethylene |
| ACC-OMe | — | 1.81 ± 0.72 | Ethylene |
| AIB | 1.68 ± 0.12 | — | Acetone, $CO_2$ |
| D-Alanine | 3.46 ± 0.51 | — | Acetaldehyde, $CO_2$ |
| Glycine | 21.4 ± 7.9 | — | $CO_2$ |

Examples 3-5 are prophetic examples.

Example 3

Closed Flower Storage

A dozen lilies are cut at similar stages of floral development. The cut end of each of 6 lilies is submerged in 100 mL of 10 mM N-methyl-ACC or ACC-NH$_2$. Alternatively, the cut ends can be submerged into 100 mL of a solution containing an appropriate concentration of α-aminoisobutyric acid (AIB), D-alanine, and glycine. Other concentrations of these inhibitor compounds may be suitable for a given plant variety, and can be determined by trial and error. The cut ends of the remaining six lilies are submerged in untreated water. The 12 lilies are placed in a cold room at 5° C. in the dark. After two weeks in the cold room, the flowers are transferred to room temperature, and the time until floral opening is measured.

Example 4

Opened Flower Storage

A dozen lilies that were previously cut and have opened within the past 24 hours are either placed in a solution of 10 mM N-methyl-ACC, 10 mM ACC-NH$_2$, or solutions containing appropriate concentrations of α-aminoisobutyric acid (AIB), D-alanine, glycine or plain water. Other concentrations of both inhibitor compounds may be suitable for a given plant variety, and can be determined by trial and error. The flowers are allowed to stand at room temperature until the flowers have noticeably wilted. The storage solutions and water are refreshed by adding fresh solution as necessary, but at most once per day.

Example 5

Fruits and Vegetables

Harvested fruits and vegetables are sprayed with a suitable concentration of N-methyl-ACC, ACC-NH$_2$, α-aminoisobutyric acid (AIB), D-alanine, glycine or water as a control. For example, 10 mM solutions of each type of cyclic inhibitor or appropriate concentrations of acyclic inhibitor can be applied. Fruits and vegetables including members of the apple family, stone fruits, avocado, citrus, berries, tomatoes, cherry tomatoes, bananas, cucurbits, grapes and other types can be treated as above. The solution of ACCO inhibitor is applied by spraying, drenching, or fogging and allowed to contact the subject produce item for a suitable amount of time before washing off. The proper concentration of ACCO inhibitor for each type of produce can be determined by trial and error. The effectiveness of inhibition on a given piece of fruit is monitored by applying the ACCO inhibitor and then testing the subject fruit item for release of ethylene gas. The inhibitor compound is tested for toxicity prior to being applied to produce items that will be used for food.

REFERENCES

The following references are hereby incorporated by reference in their entirety.

Barlow, J. N., Zhang, Z., John, P., Baldwin, J. E., Schofield, C. J. (1997) *Biochemistry* 36, 3563-3569.
Bregoli, et al. (2002) *Physiologia Plantarum,* 114(3), 472-481.
Brunhuber, N. M., Mort, J. L., Christoffersen, R. E., Reich, N. O. (2000) *Biochemistry* 39, 10730-10738.
Dong, J. G., Fernández-Maculet, J. C., Yang, S. F. (1992) *Proc. Natl. Acad. Sci. USA* 89, 9789-9793.
Fernández-Maculet, J. C., Dong, J. G., Yang, S. F. (1993) *Biochem. Biophys. Res. Commun.* 193, 1168-1173.
Gibson, E, J., Zhang, Z., Baldwin, J. E., Schofield, C. J. (1998) *Phytochem.* 48, 619-624.
Griller, D., Ingold, K. (1980) *Acc. Chem. Res.* 13, 317-323.
Holme, E., Lindstedt, s., Nordin, I. (1982) *Biochem. Biophys. Res Commun.* 107, 518-524.
Liu, Y., Su, L.-Y., Yang, S. F. (1984) *Planta* 161, 439-443.
Liu, A., Ho, R. Y. N., Que, L. Jr. (2001) *J. Am. Chem. Soc.* 123, 5126-5127.
Price, J. C., Barr, E. W., Tirupati, B., Bollinger, J. M. Jr., Krebs, C. (2003) *Biochemistry* 42, 7497-7508.
Rocklin, A. M., Tierney, D. L., Kofman, V., Brunhuber, N. M. W., Hoffman, B. M., Christoffersen R. E., Reich, N. O., Lipscomb, J. D., Que, L. Jr. (1999) *Proc. Natl. Acad. Sci. USA* 96, 7905-7909.
Rocklin, A. M., Kato, K., Liu, H.-W., Que, L. Jr., Lipscomb, J. D. (2004) *J. Biol. Inorg. Chem.* 9, 171-182.
Solomon, E. I., Burnold, T. C., Davis, M. I., Kemsley, J. N., Lee, S.-K., Lehnert, N., Neese, R., Skulan, A. J., Yang, Y.-S., Zhou, J. (2000) *Chem. Rev.* 100, 235-349.
Su, Z., Falvey, D. E., Yoon, U. C., Mariano, P. S. (1997) *J Am. Chem. Soc.* 119, 5261-5262.
Thrower, J. S., Blalock, R. 3$^{rd}$, Klimnan, J. P. (2001) *Biochemistry* 40, 9717-9724.
Vaidyanathan, G., Wilson, J. W. (1989) *J. Org. Chem.* 54, 1815-1820.
Zhang, W., Yeh, S.-R., Hong, S., Freccero, M., Albini, A., Falvey, D. E., Mariano, P. S. (1994) *J. Am. Chem. Soc.* 116, 4211-4220.
Zhang, Z., Schofield, C. J., Baldwin, J. E., Thomas, P., John, P. (1995) *Biochem. J.* 307, 77-85.

All references, patents, and patent application described herein are incorporated herein in their entirety to the same extent as though each reference, patent and patent application had been individually incorporated by reference.

What is claimed is:

1. A method of inhibiting ethylene production in a plant or plant part, the method comprising:
   contacting the plant or plant part with an effective amount of an ACC derivative having the formula:

wherein
R$_1$ and R$_7$ are independently selected from H, substituted or unsubstituted C$_1$-C$_6$ alkyl, substituted or unsubstituted C$_3$-C$_8$ cycloalkyl, substituted or unsubstituted C$_6$-C$_{10}$ aryl, substituted or unsubstituted C$_6$-C$_{14}$ aralkyl, substituted or unsubstituted C$_4$-C$_9$ heteroaryl, or substituted or unsubstituted C$_4$-C$_9$ heterocycloalkyl;
R$_2$ is —OH, —NH$_2$, substituted or unsubstituted C$_1$-C$_6$ alkyl, substituted or unsubstituted C$_3$-C$_8$ cycloalkyl, substituted or unsubstituted C$_6$-C$_{10}$ aryl, substituted or unsubstituted C$_6$-C$_{14}$ aralkyl, substituted or unsubstituted C$_4$-C$_9$ heteroaryl, or substituted or unsubstituted C$_4$-C$_9$ heterocycloalkyl, —OR$^3$, —NR$^4$R$^5$, or —SR$^6$, except R$_2$ is not —OH when R$_1$ is H and R$_7$ is H;
R$^3$ is —H, substituted or unsubstituted C$_1$-C$_6$ alkyl, substituted or unsubstituted C$_3$-C$_8$ cycloalkyl, substituted or unsubstituted C$_6$-C$_{10}$ aryl, substituted or unsubstituted C$_6$-C$_{14}$ aralkyl, substituted or unsubstituted C$_4$-C$_9$ heteroaryl, or substituted or unsubstituted C$_4$-C$_9$ heterocycloalkyl;
R$^4$, R$^5$ and R$^6$ are independently selected from the group consisting of —H, substituted or unsubstituted C$_1$-C$_6$ alkyl, substituted or unsubstituted C$_3$-C$_8$ cycloalkyl, substituted or unsubstituted $C_6$-$C_{10}$ aryl, substituted or unsubstituted $C_6$-$C_{14}$ aralkyl, substituted or unsubstituted $C_4$-$C_9$ heteroaryl, or substituted or unsubstituted $C_4$-$C_9$ heterocycloalkyl; and wherein said of $R_1$, $R_2$ or $R_7$ is a heteroaryl selected from the group consisting of pyrrolyl, imidazolyl, pyrazolyl, isothiazolyl, isoxazoyl, pyridyl, pyrazinyl, pyrimidineyl, furyl, and thienyl.

2. The method of claim 1, wherein the substituted $C_1$-$C_6$ alkyl, substituted $C_3$-$C_8$ cycloalkyl, substituted $C_6$-$C_{10}$ aryl, substituted $C_6$-$C_{14}$ aralkyl, substituted $C_4$-$C_9$ heteroaryl, and substituted $C_4$-$C_9$ heterocycloalkyl, are independently substituted with one or more groups selected from halo, hydroxyl, amino, cyano, and lower alkoxy.

3. The method of claim 2, wherein the substituted $C_1$-$C_6$ alkyl, substituted $C_3$-$C_8$ cycloalkyl, substituted $C_6$-$C_{10}$ aryl, substituted $C_6$-$C_{14}$ aralkyl, substituted $C_4$-$C_9$ heteroaryl, and substituted $C_4$-$C_9$ heterocycloalkyl, are independently substituted with one or more groups selected from halo, hydroxyl, and methoxy.

4. The method of claim 1, wherein $R_1$ and $R_7$ are independently selected from H; unsubstituted $C_1$-$C_6$ alkyl; unsubstituted $C_3$-$C_6$ cycloalkyl; unsubstituted $C_6$-$C_{10}$ aryl; unsubstituted $C_6$-$C_{14}$ aralkyl; unsubstituted $C_4$-$C_9$ heteroaryl; and unsubstituted $C_4$-$C_9$ heterocycloalkyl; and $R_2$ is —OH, —NH$_2$, unsubstituted $C_1$-$C_6$ alkyl; unsubstituted $C_3$-$C_6$ cycloalkyl; unsubstituted $C_6$-$C_{10}$ aryl; unsubstituted $C_6$-$C_{14}$ aralkyl; unsubstituted $C_4$-$C_9$ heteroaryl; unsubstituted $C_4$-$C_9$ heterocycloalkyl; —OR$^3$, —NR$^4$R$^5$, or —SR$^6$; where R$^3$ is —H, unsubstituted $C_1$-$C_6$ alkyl; unsubstituted $C_3$-$C_6$ cycloalkyl; unsubstituted $C_6$-$C_{10}$ aryl; unsubstituted $C_6$-$C_{14}$ aralkyl; unsubstituted $C_4$-$C_9$ heteroaryl; or unsubstituted $C_4$-$C_9$ heterocycloalkyl; and R$^4$, R$^5$ and R$^6$ are independently selected from —H, unsubstituted $C_1$-$C_6$ alkyl; unsubstituted $C_3$-$C_6$ cycloalkyl; unsubstituted $C_6$-$C_{10}$ aryl; unsubstituted $C_6$-$C_{14}$ aralkyl; unsubstituted $C_4$-$C_9$ heteroaryl; and unsubstituted $C_4$-$C_9$ heterocycloalkyl.

5. The method according to claim 1, wherein $R_7$ is —H.

6. The method according to claim 1, wherein the heteroaryl is elected from the group consisting of pyrrolyl, pyridyl, and thienyl.

7. The method according to claim 6, wherein the heteroaryl is pyrrolyl.

8. The method according to claim 1, wherein $R_2$ is hydroxyl, amino, or lower alkoxy.

9. The method according to claim 8 wherein $R_2$ is hydroxyl, —NH$_2$, or methoxy.

10. The method according to claim 1, wherein $R_7$ is —H and $R_1$ is —H or lower alkyl.

11. The method of claim 10, wherein $R_1$ is —H or methyl.

12. The method of claim 1, wherein the plant or plant part is a fruit, a vegetable, a leaf, a branch, a flower, a root or a stem.

* * * * *